United States Patent [19]
Yamaguchi et al.

[11] Patent Number: 5,393,400
[45] Date of Patent: Feb. 28, 1995

[54] COMPONENT SENSOR FOR MOLTEN METALS

[75] Inventors: Shu Yamaguchi, Nagoya; Norihiko Fukatsu, Tajima; Hideo Kimura, Kyoto, all of Japan

[73] Assignee: Yamari Sangyo Kabushiki Kaisha, Osaka, Japan

[21] Appl. No.: 789,489

[22] Filed: Nov. 8, 1991

[30] Foreign Application Priority Data

Dec. 29, 1990 [JP] Japan .................. 2-416898

[51] Int. Cl.$^6$ .......................................... G01N 27/411
[52] U.S. Cl. .................................. 204/413; 204/422
[58] Field of Search ........ 204/153.1, 153.18, 421–429, 204/433, 413

[56] References Cited

U.S. PATENT DOCUMENTS

| | | | |
|---|---|---|---|
| 3,205,158 | 9/1965 | Renier | 204/153.1 |
| 3,705,089 | 12/1972 | Grubb | 204/435 |
| 3,714,014 | 1/1973 | Romberger et al. | 204/412 |
| 3,794,569 | 2/1974 | Kawai et al. | 204/422 |
| 4,492,614 | 1/1985 | Welsh | 204/427 |
| 4,601,810 | 7/1986 | Tiwari et al. | 204/413 |
| 4,645,571 | 2/1987 | Dubreuil et al. | 204/422 |
| 4,902,402 | 2/1990 | Pebler et al. | 204/427 |

FOREIGN PATENT DOCUMENTS 2179420 11/1973 France .

OTHER PUBLICATIONS

Acta Metallurgica, vol. 2, No. 4, pp. 621–631, Jul. 1954.
Abstract of JP 51-136532 (World Patents Index) Nov. 27, 1976.
Abstract of JP 57-047858 (World Patents Index) Mar. 18, 1982.
Abstract of JP 1-177437 (Patent Abstract of Japan) Jul. 13, 1989.

*Primary Examiner*—T. Tung
*Attorney, Agent, or Firm*—Adduci, Mastriani, Schaumberg & Schill

[57] ABSTRACT

A metal melt is used as a measuring electrode while a pure form of a particular metal component to be measured or an alloy containing it is used as a standard electrode. The active substance to come in contact with the standard electrode includes at least one halide of an alkali halide and an alkaline earth halide, both having ion conductivity, and a halide of the particular metal component, any one of such halides consisting of a solid phase and a liquid phase. This active substance is provided such that it can come into contact with the metal melt and is used as an electrolyte as well. It is thus possible to provide a continuous detection of the concentration of the particular component in the molten metal to be measured.

4 Claims, 3 Drawing Sheets

COMPONENT SENSOR FOR MOLTEN METALS

BACKGROUND OF THE INVENTION

The present invention relates to a chemical cell type of component sensor for detecting the concentration of a specific component contained in a metal melt and, more particularly, to a component sensor for high-temperature purposes, which uses a composite molten salt electrolyte consisting of a solid phase and a liquid phase. The term "metal melt" as used herein is understood to mean the melt of a metal or alloy.

In producing galvanized steel plates for industrial purposes, esp., automotive purposes by hot dip coating, a small amount of aluminum is being now generally added to zinc for improving their quality. A general purpose of adding aluminum is to improve the adhesion between the steel plates and zinc. In this galvanized steel plate production line, an aluminum mother alloy is fed into a molten zinc bath for hot dip coating to regulate the concentration of aluminum in the molten zinc bath. Then, the steel plate is coated with zinc by hot dip coating. In order to place post-steps under proper control, it is desired to provide a successive detection of the content of aluminum in the molten zinc bath, thereby achieving intermediate and proper automatic control of the concentration of aluminum in the molten zinc bath.

Conventional means for detecting the concentration of a specific component in this type of molten metal has involved sampling a part of the molten metal bath intermittently, solidifying it—followed by its dissolution in an acid to form an aqueous solution, and analyzing this aqueous solution by ordinary chemical analysis or atomic-absorption spectroscopy. It has been reported that, for scientific purposes, the activity (or concentration) of alloy components can be made electrochemically with a molten salt electrolyte—see "Acta Metallurgica", 2, pp. 621-631 (1954).

For such conventional techniques, however, it is required to sample out a part of the molten metal bath. This makes it impossible to make an in-situ measurement of the concentration of a particular component and so needs much labor and time to determine that concentration. Another problem is that difficulty is involved in reducing the regulation of component concentrations in the molten metal bath to automation. In other words, complicated analytical procedures are needed for determining the concentration of the particular component after a part of the metal melt has been sampled out, and a considerable length of time is required until the results of analysis are available. The above-mentioned report on measuring the activity of alloy components is directed to using a molten salt electrolyte rather than a solid electrolyte.

Having been accomplished to seek a solution to such problems, the present invention has for its object to provide a component sensor for molten metals, which can continuously detect the concentration of a particular component in a molten metal by electrical signals, can be used at relatively high temperatures, say, 420°-800° C. and has high resolving power in a wide concentration range.

SUMMARY OF THE INVENTION

According to one aspect of this invention, the above-mentioned object is achieved by the provision of a chemical cell type of component sensor for detecting the concentration of a particular metal in a metal melt, wherein said metal melt is used as a measuring electrode and a pure form of said particular metal or an alloy containing said particular metal is used as a standard electrode. An active material to come into contact with the standard electrode and capable of coming into contact with the metal melt includes at least one halide of an alkali metal or an alkali earth metal, or a mixture thereof, each having ion conductivity, and a halide of said particular metal, any one of said halides comprising a solid phase component and a liquid phase component.

The component sensor for molten metals according to this invention uses said active material to convert a chemical potential change of the particular metal into a chemical potential change of the alkali or alkaline earth metal, and said active substance consisting of a mixture of a solid salt and a molten salt which is used as a composite electrolyte partition to construct a chemical cell where the ions of said alkali or alkaline earth metal serve as charge carriers.

According to the first aspect of this invention, the metal melt detectable by this component sensor may preferably but not exclusively be selected from the group consisting of zinc, solder and copper. More preferably or according to another aspect of this invention, that metal melt is a zinc melt.

According to the first aspect of this invention, the aforesaid particular metal may preferably but not exclusively be at least one metal element selected from the group consisting of aluminum, cadmium, antimony, iron and lead. More preferably or according to a third aspect of this invention, that particular metal is aluminum.

According to a fourth aspect of this invention, there is provided a component sensor as recited in the first aspect, which includes a protecting tube which has no electron conductivity and in which said standard electrode and said active material are tightly enclosed, a projection attached to the tip of said protecting tube, which is removable by snapping in use, and an electrically conductive holder which is designed to hold said protecting tube and is capable of coming into electrical contact with said metal melt. Note that the protecting tube carries a halide mixture of high hygroscopicity.

According to a fifth aspect of this invention, there is provided a regulator arrangement for regulating the components of a metal melt, including said component sensor for molten metals, which is immersed in said metal melt; a control circuit for receiving a detection signal from said component sensor and calculating the target amount of said particular metal component to be added to said metal melt on the basis of said received signal, and feeder means for adding the said particular metal component to said metal melt on the basis of the result of said calculation made by said control circuit.

BRIEF DESCRIPTION OF THE DRAWINGS

The present invention will now be described in greater detail, by way of example alone, with reference to the accompanying drawings in which.

PREFERRED EMBODIMENT OF THE INVENTION

The action of the component sensor for molten metals according to this invention will now be explained with reference to a chemical cell structure expressed by the following cell scheme:

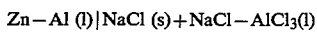

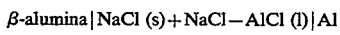

wherein Zn—Al (l) stands for molten zinc containing aluminum to be measured, NaCl (s)+NaCl—AlCl$_3$ (l) represents a mixed molten salt of NaCl—AlCl$_3$ saturated with solid NaCl, and Al indicates pure aluminum used as the standard electrode. The mixed molten salt of NaCl-AlCl$_3$ saturated with solid NaCl, used as the active substance, is a good Na ion conductor. Since the NaCl of the mixed molten salt of NaCl—AlCl$_3$ has been saturated, the activities of NaCl and AlCl$_3$ are kept constant. Hence, if the activity of aluminum at both electrodes is determined, then the activity of Na at both electrodes is determined by the following reaction scheme:

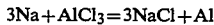

Thus, an Na concentration cell is constructed.

An electromotive force E of this Na concentration cell has the following relations with the activity or concentration of Al:

$$E = -RT/3F \times \ln (a_{Al}/a_{Al'}) = 2.303 RT/3F \times (\log (wt\%Al) + Const.)$$

wherein $a_{Al}$ is the activity of aluminum in the molten zinc, $a_{Al'}$ is the activity of aluminum in the standard electrode, wt%Al is the weight % of aluminum in the molten zinc, and Const. is constant determined by the coefficient of activity of aluminum and the activity of aluminum at the standard electrode.

From this, it is possible to find the concentration of aluminum in the molten zinc by measuring the electromotive voltage.

In this embodiment, β-alumina is used as a partitioning membrane for separating both the electrodes from each other. However, when the metal components in the molten metal do not dissolve in the mixed molten salt phase of the electrolyte or when there is no fear that the mixed molten salt forming the electrolyte may vary in composition, the β-alumina partition may be dispensed with.

The present invention will now be described at great length with reference to the following examples.

EXAMPLE 1

In this example, the first embodiment of a chemical cell type of sensor for detecting aluminum in molten zinc is explained.

Figure 1:
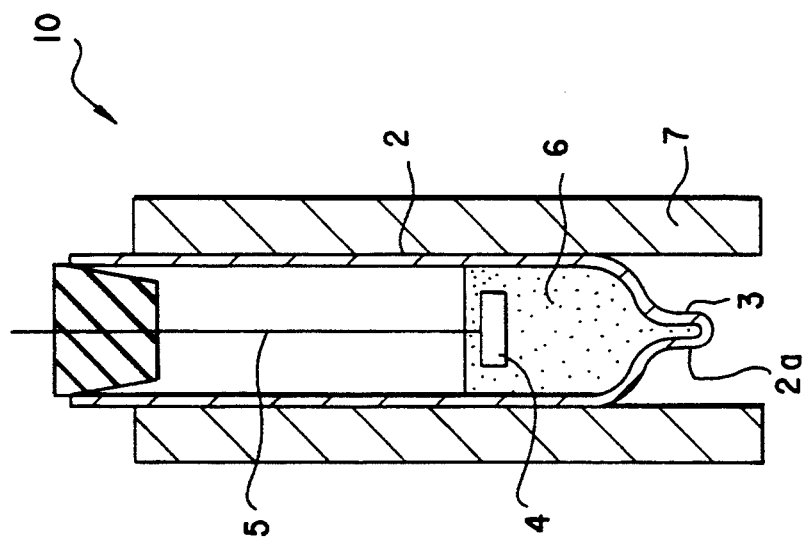
FIG. 1 is a schematic section showing one embodiment of the component sensor according to this invention.

As shown in FIG. 1, a component sensor generally shown by 1 includes a container 2 in a bottomed cylindrical form, which is provided at its tip with a detachable-by-snapping projection 3. The container 2 may be built up of, e.g. quartz or pyrex and is filled therein with, for instance, electrolytes 6a and 6b consisting of a mixed molten salt of NaCl-AlCl$_3$ saturated with solid NaCl. The container 2 is provided to prevent the mixed molten salt of NaCl—AlCl$_3$ filled therein from flowing out. Inserted into the electrolyte 6a is a pure aluminum sheet 4 acting as a standard electrode, with which a lead 5 of pure aluminum is connected. As illustrated, the container 2 is supported by a protecting tube 7 which may be built up of, e.g. graphite or a heat-resistant alloy. The protecting tube 7 is also used as an electrode lead on the molten zinc side.

Packed around the pure aluminum sheet 4, the mixed molten salt electrolyte 6a of NaCl—AlCl$_3$ is isolated from the surrounding mixed molten salt electrolyte 6b by a partition 8 formed of β-alumina. This is provided to prevent molten zinc from penetrating through the tip 2a of the container 2 into the mixed molten salt of NaCl—AlCl$_3$ surrounding the alumina sheet 4 when the component sensor 1 is used, causing the zinc or aluminum in the molten zinc to dissolve in the mixed molten salt phase of NaCl—AlCl$_3$ and so vary its composition. In other words, when the concentration of Al in the zinc melt is low, the aluminum is replaced by the zinc, as represented by the following reaction scheme:

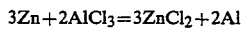

causing the molten salt to vary in composition with an increase in the amount of zinc chloride. It is the β-alumina partition which prevents such variation from occurring. Also, the β-alumina partition 8 serves well to prevent any incidental influence from being induced by a lowering of the ion transference number due to the substitution of the molten salt by impurities. Note that the partition 8 may be formed of other materials, provided that they are stable sodium ion conductors.

In using the component sensor 1, the projection 3 is removed by snapping so that the tip 2 of the container 3 can be immersed in a zinc melt bath. For measurement, an electromotive voltage occurring between the lead 5 and the lead of the protecting tube 7 is found by a voltmeter, not shown.

Reference will now be made to the experimental data.

Figure 3:
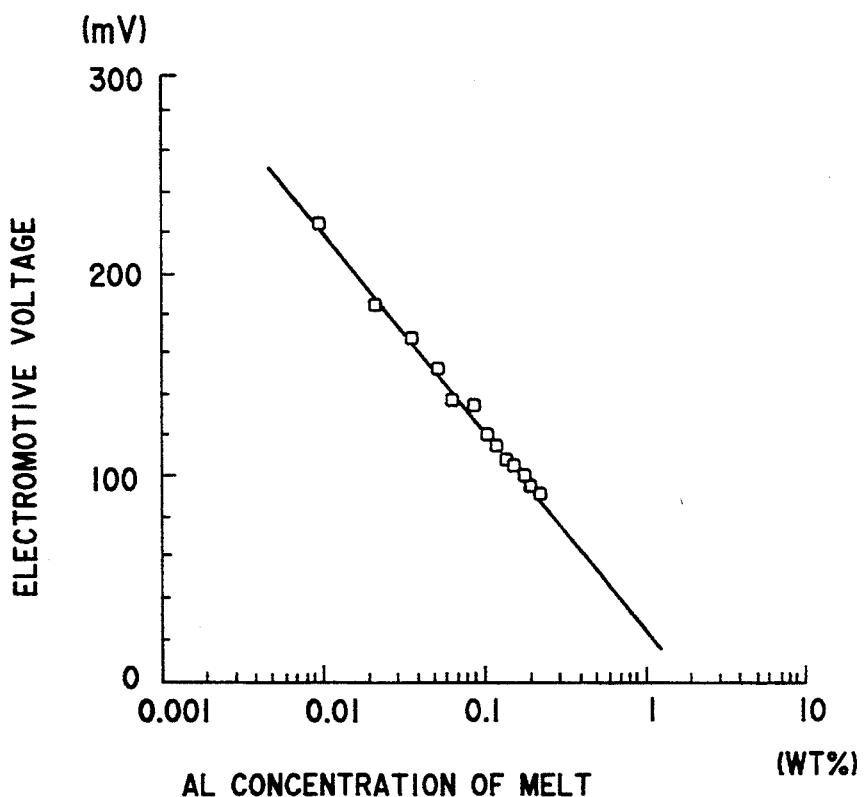
FIG. 3 is a characteristic diagram showing the relation between the concentration of aluminum in a molten zinc bath and the electromotive voltage in the first embodiment.

With the component sensor 1 embodying this invention, the concentration of aluminum in a zinc melt was measured. The component sensor 1 was first immersed in 2 kg of molten zinc in its pure form, stored in a graphite crucible. Then, pure aluminum was added to the molten zinc to measure the resulting electromotive voltages in varied aluminum concentrations. The results are illustrated in FIG. 3. As can be seen from FIG. 3, the logarithm of the electromotive voltage and aluminum concentration obviously shows a linear relation, indicating that the concentrations of aluminum could be measured with sufficiently high accuracy.

Figure 4:
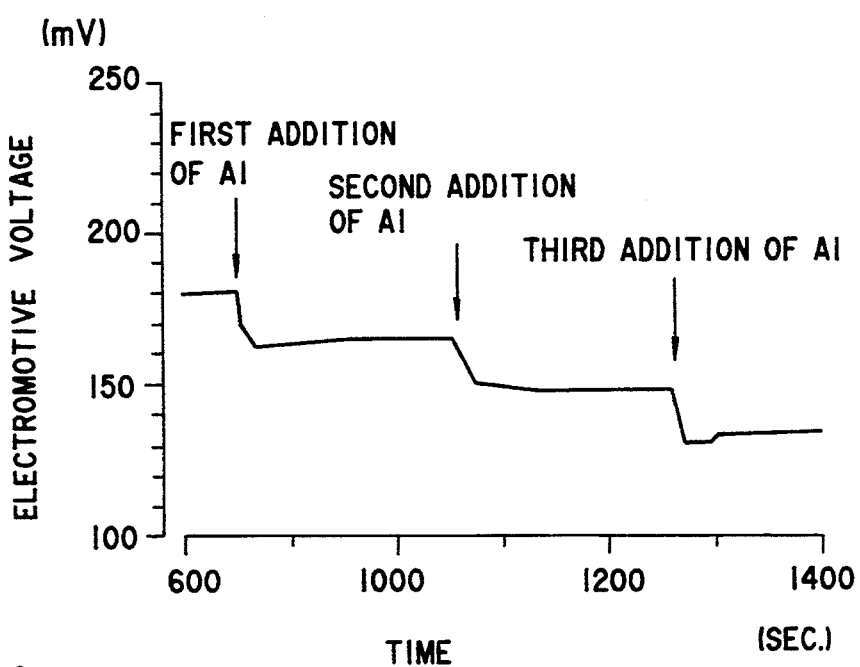
FIG. 4 is a characteristic diagram showing the relation between the time and the electromotive voltage when aluminum is added to a zinc melt.

FIG. 4 shows how the electromotive voltage changes with time, when some batches of aluminum are added at suitable intervals to a zinc melt bath. As can be understood from FIG. 4, the electromotive voltage changes drastically whenever one batch of aluminum is added to zinc melt bath, and remains well stabilized until the next batch is added.

The component sensor 1 for zinc hot dipping, using such a composite molten salt electrolyte, can be well used in a temperature range of a certain low temperature to up to around 800° C. under NaCl saturation conditions, because the NaCl—AlCl$_3$ (ZnCl$_3$)-based composite molten salt electrolyte consists of a ternary eutectic crystal structure whose eutectic temperature is as low as about 100° C. This component sensor 1 can thus be effectively used to provide an in-situ continuous detection of aluminum concentrations of 0 to some thousand ppm at any desired position in molten zinc at a temperature of about 150° to 800° C. within an error of some two-digit ppm.

EXAMPLE 2

Figure 2:
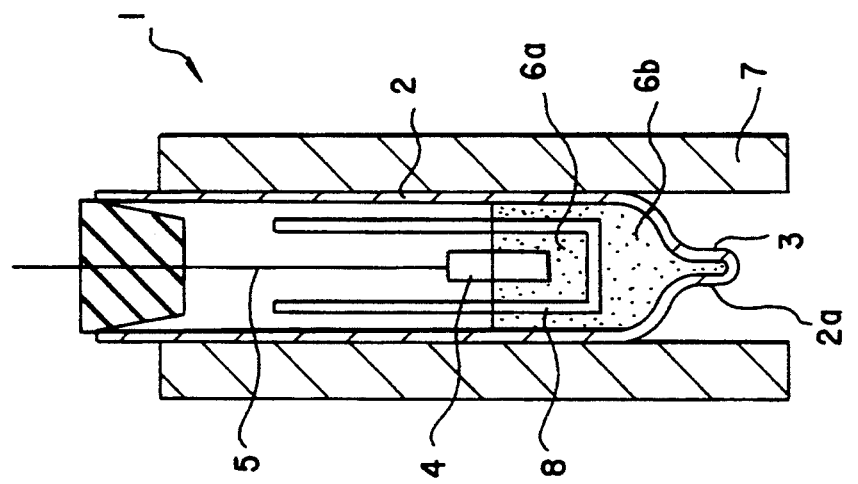
FIG. 2 is a schematic section showing another embodiment of the component sensor according to this invention.

FIG. 2 illustrates the second embodiment of the component sensor according to this invention.

In FIG. 2, parts that are substantially identical with those shown in FIG. 1 are referred to by the same reference numerals and so will not be explained.

A component sensor 10 according to the second embodiment is a modification of the first component sensor 1, wherein the partition 8 is removed from within the mixed molten salt electrolyte 6 shown in FIG. 1. This component sensor 10, because of the absence of the partition 8, is effectively used especially when the compositional variation of the mixed molten salt electrolyte 6 is considered to be negligible within a measuring period of time.

Other embodiments may be envisioned, wherein the ratio of solid NaCl to be mixed with the mixed molten salt electrolyte packed in the container is regulated to minimize the ratio of the liquid-phase molten salt relative to the solid-phase salt, thereby enabling the component sensor to have a strength close to that of the solid electrolyte with the strength that the solid-phase salt itself possesses and making it easy to handle the component sensor due to its quasi-solid state. In place of the Na salt in the aforesaid mixed molten salt electrolyte, use may be made of Li, K and other salts.

EXAMPLE 3

Figure 5:
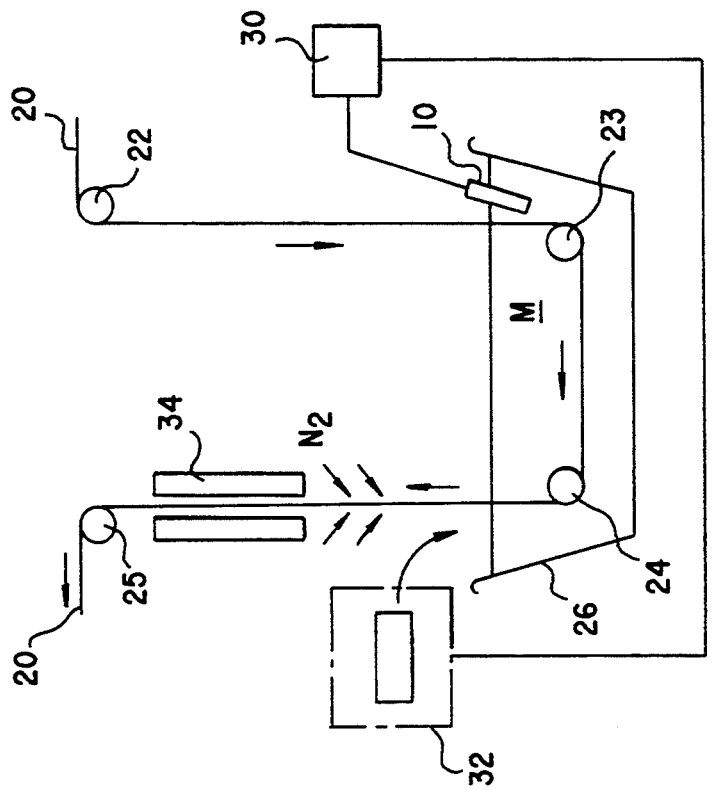
FIG. 5 is a schematic view showing one example of using the component sensor, which is a third embodiment of this invention.

FIG. 5 shows the 3rd embodiment of the component sensor according to this invention, which is designed such that an automatic regulation of the concentration of aluminum in a zinc melt bath is achieved with the aforesaid component sensor.

Referring to FIG. 5, a thin steel plate 20 is carried through rollers 22, 23, 24 and 25 in the direction shown by an arrow. While carried by the rollers 23 and 24, the steel plate 20 is being immersed in a zinc melt bath M located in a tank 26. Upon being guided up from the bath M, N$_2$ gas is blown onto the steel plate, which is then thermally treated through a heat-treatment furnace 34 to enhance the adhesion of zinc thereto. A detection signal from the component sensor 10, immersed in the zinc melt bath M, is sent to a controller 30, which, on the basis of this input signal, in turn calculates the target weight of an aluminum-containing ingot to be added to the zinc melt bath M. On the basis of the result of this calculation, the controller 30 outputs to an aluminum feeder 32 a signal for the weight of the aluminum-containing ingot to be fed into the zinc melt bath M. In response to this signal, the feeder 32 introduces the aluminum-containing ingot into the zinc melt bath M. In this way, the concentration of aluminum in the zinc melt bath M can be regulated automatically.

According to the 3rd embodiment of this invention, the concentration of aluminum in the zinc melt bath M can be put under continued control to make the zinc coated onto the surface of the steel plate homogeneous; it is possible to prevent the coated zinc from peeling off or cracking during post-treatments, thus assuring that the zinc remains well coated onto the steel plate.

EXAMPLE 4

Figure 6:
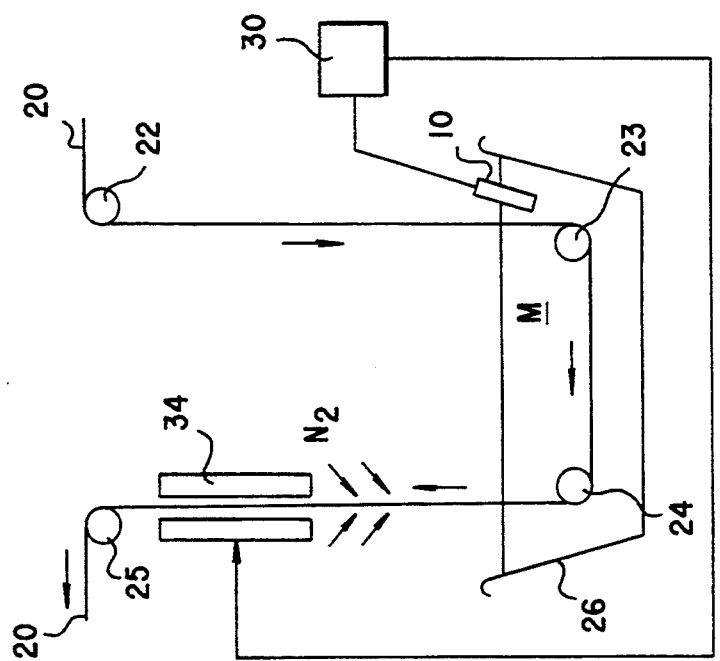
FIG. 6 is a schematic view showing another example of using the component sensor, which is a fourth embodiment of this invention.

FIG. 6 illustrates the 4th embodiment of this invention, according to which the heating temperature of the heat-treating furnace is automatically controlled in response to a sensor signal. In FIG. 6, parts that are substantially identical with those shown in FIG. 5 are referred to by the same reference numerals and so will not be explained.

The controller 30 calculates at what temperature the steel plate 20 should be thermally treated in the heat-treating furnace 34 in response to the signal sent from the component sensor 10 to it, and outputs the resulting signal to the heat-treating furnace 34. In response to this signal, the heat-treating furnace 34 controls the heating temperature to heat the steel plate 20. For instance the inside temperature of the heat-treating furnace 34 is controlled primarily depending upon a change in the surface state of the zinc coated onto the surface of the steel plate, which is mainly caused by a change in the concentration of aluminum in the zinc melt bath M. Thus, the zinc remains uniformly well coated onto the surface of the steel plate 20.

By choice of a suitable combination of some types of molten salt electrolytes, the component sensor of this invention can be applied to detecting not only aluminum but other metal elements as well. It is understood that this component sensor may be designed either as a disposable spot type that can be thrown away after use or as a continuously usable type for automatic control purposes.

As mentioned above, the present component sensor for molten metals can successfully provide a continuous detection of the concentration of a particular component in molten metals by means of electrical signals and can be well used at a relatively high temperature range of 420° to 800° C. with high resolving power in a wide concentration range.

With the present component sensor for molten metals, it is possible to obtain surface-treated steel plates having high strength and processability as well as increased service life by placing the additive feeder and heat-treating furnace or other equipment under continued control through the detection of components therewith.

We claim:

1. A chemical cell component sensor for detecting a particular component contained in a metal melt by measuring an electromotive voltage occurring between said metal melt as a measuring electrode and a standard electrode, the component sensor comprising:

a holder used as the lead for the measuring electrode;
   a protecting tube housed within said holder, said protecting tube having a cylindrical bottomed surface, no electron conductivity and a projection provided at a tip portion of the bottomed surface, said projection being removable by snapping;

an active substance in said protecting tube and consisting essentially of a first halide which consists of at least one halide of an alkali metal and at least one halide of an alkaline earth metal, said first halide consisting of both a solid phase and a liquid phase when said sensor is in contact with said metal melt, and a second halide of the particular component to be detected, said active substance being saturated with said first halide;

a standard electrode which is a pure form of the particular component to be detected or is an alloy containing the particular component to be detected; and a partition within said protecting tube for enclosing said standard electrode and a portion of said active substance;

the standard electrode being in contact with the active substance in said protecting tube.

2. A component sensor as claimed in claim 1, wherein said metal melt is a zinc melt.

3. A chemical cell component sensor for detecting aluminum contained in a metal melt by measuring an electromotive voltage occurring between said metal melt as a measuring electrode and a standard electrode, the component sensor comprising:

a holder used as the lead for the measuring electrode;

a protecting tube housed within said holder, said protecting tube having a cylindrical bottomed surface, no electron conductivity and a projection provided at a tip portion of the bottomed surface, said projection being removable by snapping;

an active substance in said protecting tube and consisting essentially of NaCl and a halide of aluminum, said NaCl consisting of both a solid phase and a liquid phase when said sensor is in contact with said metal melt, said active substance being saturated with said NaCl;

a standard electrode which is a pure form of aluminum or is an alloy containing aluminum; and a partition within said protecting tube for enclosing said standard electrode and a portion of said active substance;

the standard electrode being in contact with the active substance in said protecting tube.

4. An arrangement for regulating the components of a metal melt, which includes:

a component sensor as recited in claim 1 or 3, which is immersed in said metal melt, a control circuit which is operated in response to a signal from said component sensor to calculate the target amount of a particular metal component to be added to said metal melt; and an additive feeder for adding said particular metal component to said metal melt on the basis of the result of said calculation made in said control circuit.

* * * * *